United States Patent
Morris, Sr. et al.

[11] Patent Number: 6,052,614
[45] Date of Patent: Apr. 18, 2000

[54] ELECTROCARDIOGRAPH SENSOR AND SENSOR CONTROL SYSTEM FOR USE WITH MAGNETIC RESONANCE IMAGING MACHINES

[75] Inventors: G. Ronald Morris, Sr.; G. Ronald Morris, Jr., both of Bay Shore, N.Y.; James W. Valentine, Spokane, Wash.

[73] Assignee: Magnetic Resonance Equipment Corp., Bay Shore, N.Y.

[21] Appl. No.: 08/938,005

[22] Filed: Sep. 12, 1997

[51] Int. Cl.⁷ .................................................. A61B 5/0402
[52] U.S. Cl. ........................... 600/509; 600/411; 128/901
[58] Field of Search .................................. 600/509, 407, 600/410, 411, 522, 520, 523; 128/901

[56] References Cited

U.S. PATENT DOCUMENTS

| | | |
|---|---|---|
| 4,694,837 | 9/1987 | Blakely et al. . |
| 4,763,075 | 8/1988 | Weigert . |
| 5,038,785 | 8/1991 | Blakely et al. . |
| 5,217,010 | 6/1993 | Tsitlik et al. ................................ 607/9 |
| 5,394,873 | 3/1995 | Kraemer et al. . |
| 5,423,863 | 6/1995 | Felblinger et al. . |
| 5,464,014 | 11/1995 | Sugahara .................................. 600/523 |
| 5,691,641 | 11/1997 | Cansell et al. . |
| 5,733,247 | 3/1998 | Fallon ...................................... 600/410 |
| 5,782,241 | 7/1998 | Felblinger et al. . |

FOREIGN PATENT DOCUMENTS 2704131  10/1994  France .

OTHER PUBLICATIONS

Patient Monitoring During MR Examination, by J. Felblinger, G. Muller, M. Kraemer, M. Lanoux and C. Boesch, undated.

Optically Powered Battery Free and Wireless System for Electrocardiogram Acquisition during MR Examinations, by M.B. Scheidegger, M. Stuber, B. Stüssi, S.E. Fischer and P. Boseiger, undated.

Electrocardiogram Acquisition during MR Examinations for Patient Monitoring and Sequence Triggering, J. Felblinger, C. Lehmann and C. Boesch, pp. 523–529, Magnetic Resonance in Medicine vol. 32 (1994).

*Primary Examiner*—Kennedy J. Schaetzle
*Attorney, Agent, or Firm*—Amster, Rothstein & Ebenstein

[57] ABSTRACT

A system for monitoring an ECG during an MRI examination which permits the monitoring system to be located near the patient and which eliminates artifacts affecting the accurate reading of the ECG. The system allows for control of lead select and battery on stand by mode and can monitor battery state and lead off conditions.

17 Claims, 2 Drawing Sheets

ELECTROCARDIOGRAPH SENSOR AND SENSOR CONTROL SYSTEM FOR USE WITH MAGNETIC RESONANCE IMAGING MACHINES

FIELD OF THE INVENTION

This invention relates to instruments for making electrocardiograms (ECG)s of patients during the performance of a magnetic resonance imaging (MRI) scan.

BACKGROUND OF THE INVENTION

Voltage artifacts, which interfere with the ECG signal presented to the ECG monitor, are common when using standard diagnostic type ECG equipment in the MRI environment. These interfering signals are induced in the patient cable and the electrode leads which connect the ECG electrodes on the patient inside the MRI machine to the ECG monitor and sequence trigger system. Two sources of these interfering signals are the radio frequency (RF) pulses and the magnetic field gradient pulses which are generated by the MRI machine. In the case of the RF pulses, they not only cause a degradation in the cardiac signal measurement, but they often set up very large electrical currents in the connecting cables and leads. These cables and leads can become very hot and burn the patient if they are in contact with the patient's skin.

A third source of voltage artifacts, known as motion artifacts, also exists. These interfering signals are picked up by induction in the connecting leads or directly from the patient through the ECG electrodes. One example of a motion artifact is caused by patient breathing. The electrode leads, which are attached to the electrodes on the patient's chest, move in the primary magnetic field of the MRI magnet. Voltages are induced in the leads as a result of lead motion and are combined with the cardiac voltage at the input to the monitor. Another example of a motion artifact is one caused by patient blood flow. Rapid blood flow in the aorta and other large heart vessels also generates interfering signals. This is due to the blood being an electrical conductor that is moving in a magnetic field. This artifact, combines with the cardiac voltage within the patient and, is picked up on the skin by the ECG electrodes.

Conversely, certain artifacts in the MRI image can result from high frequency signals generated by ECG electronics. These signals are radiated as electromagnetic waves to the MRI machine through the patient cable and the electrode leads which act as transmitting antennas. These artifacts degrade the MRI image. Placement of the electronics can also effect the MRI imaging by obscuring a particular area.

A device for monitoring ECG's and respiration in an MRI setting, while minimizing artifacts is described in U.S. Pat. No. 4,763,075. An electronic sensor module, including an RF filter, amplifier stage and slew rate filter, which filters RF and interfering pulses from the ECG and respiration signals is located outside the MRI tunnel. This filtered signal is transmitted to a patient monitor located outside of the MRI shielded room through optic cables to avoid any further interference by the MRI. One disadvantage of the system described in U.S. Pat. No. 4,763,075 is the need to use long cables and leads because the electronics sensor module is located outside of the MRI tunnel. This can result in a very large electrical current being generated in the long cables and leads, which can become very hot and burn the patient. In addition, the long cables can generate a field which can also interfere with the MRI image. Another disadvantage of this device is the difficulty of monitoring an unstable patient since the ECG monitor must be outside of the MRI shielded room. A further disadvantage of this system is the inability to control the selection of the active leads of the ECG, and the inability to monitor a "lead-off" condition.

Another device for monitoring ECG's in an MRI setting, while attempting to minimize artifacts is described in French Patent National Registration No. 930491. The electronic sensor module of the device described in this reference is designed to be used within the MRI tunnel. However, it includes electrodes rigidly attached to the module which is strapped directly onto the patient. A disadvantage of this device is that the entire module must be placed close to the heart for monitoring the patient's ECG. This arrangement can obscure the heart and other areas from MRI imaging and has little effect on minimizing motion artifacts, specifically those artifacts due to the blood flow. In addition, there is no remote control of the active leads of the ECG. Furthermore, this device does not include a slew-rate filter for suppressing voltage spikes and gradient pulses picked up by the electrode leads. In addition, no provision is made for monitoring a lead-off condition or the battery charge state of the device.

Other devices for monitoring ECG's in an MRI setting, while attempting to minimize artifacts are described in U.S. Pat. Nos. 4,694,837 and 5,038,785. The electronic sensor modules described in these references are designed to be used within the MRI tunnel. However, there is no remote control of the active leads of the ECG. In addition, there is no provision for monitoring a lead off condition or the battery charge state of the device.

It is therefore an objective of the present invention to provide a system for reducing voltage artifacts during the making of ECG's while using MRI's.

It is another objective of the present invention to provide a system for reducing motion artifacts during the making of ECG's while using MRI's.

It is yet a further objective of the present invention to allow remote control and monitoring of the system during the making of ECG's to allow for the best output signal.

It is yet another objective of the present invention to provide a system that can be moved to prevent the obscuring of body parts from MRI imaging.

SUMMARY OF THE INVENTION

The invention relates to a system for making ECG's of patients during the performance of an MRI scan. The system includes an ECG electronics sensor module comprising at least three commercially available, disposable ECG electrodes for connecting to the patient's skin. Short, high resistance leads connect the electrodes to an electronic circuit which is shielded, from the RF field generated by the MRI, by a Faraday shield. The electronic circuit is located on, or in close proximity to, the patient, allowing optimal positioning of the circuit and electrodes. An RF filter is provided for each lead at the entrance to the Faraday shield. A monitor and control system is provided which is used to monitor the ECG and other functions of the system such as a lead off condition and battery voltage state and can be used to select pairs of active leads and control the battery state, turning it to on or to stand-by. This arrangement of components minimizes voltage and motion artifacts associated with making ECG's during the performance of an MRI scan and provides greater flexibility in the monitoring and control of the system.

More specifically, the individual ECG electrodes are connected by short, high resistant leads to the electronics sensor module which is powered by a non-magnetic battery.

These leads are connected to an RF filter, the output of which is connected to a lead select network. The lead select network is controlled to select pairs of leads to provide the best output signal. The pair of active leads are connected to a wide band (0.1 Hz.–10 kHz., minimum) low gain differential preamplifier, the output of which is connected to a single ended higher gain, wide band amplifier. A status encode circuit is coupled between the output of the wide band amplifier and an input of the differential amplifier. A DC voltage offset produced by the status encode circuit is preferrably controlled based on the charge state of the battery, the lead combination selected and a lead off condition. The output of the wide band amplifier is preferrably coupled to a slew-rate filter which discriminates against gradient pulse noise. The amplified cardiac signal, essentially free of RF and gradient pulse noise, along with the specific DC offset is input to a pulse width modulator that drives a fiber optic transmitter. The resulting light beam, modulated by the cardiac signal and the DC voltage offset, exits the ECG electronics sensor module and the MRI magnet tunnel on a fiber optic cable and is received at some other location in the shielded room by a fiber optic receiver in an ECG monitor. After conversion to an electrical voltage, the signals are demodulated and processed in the ECG monitor which displays the ECG signal. The monitor also produces control signals for remote control of the battery state and selection of pairs of active lead in the ECG electronics sensor module. These control signals are input to a fiber optic transmitter which modulates a light beam to transmit these signals to the ECG electronics sensor module via a second fiber optic cable. The ECG electronics sensor module includes a fiber optic receiver which convert the light beam back to electrical signals establishing two way communications between the ECG electronic sensor module and the monitor.

BRIEF DESCRIPTION OF THE DRAWINGS

These and other objects and advantages of the invention, as well as the details of the illustrative embodiments, will be more fully understood by reference to the following portion of the specification, taken in conjunction with the accompanying drawings, in which.

DESCRIPTION OF A PREFERRED EMBODIMENT

Figure 1:
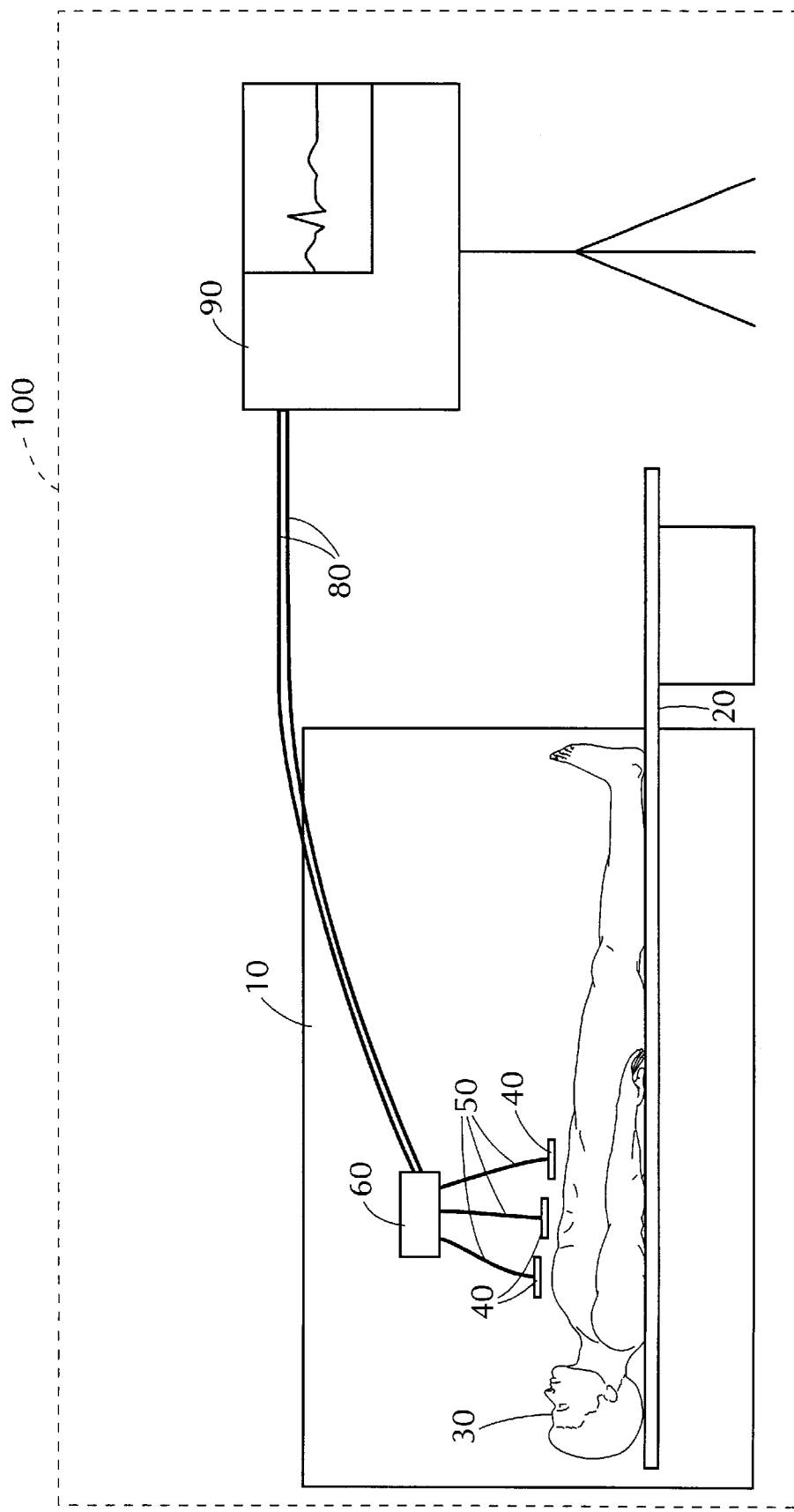
FIG. 1 is a block diagram of the invention.

Referring to FIG. 1, an MRI tunnel 10 with patient bed 20 is shown inside a shielded room 100. Three electrodes 40 are attached to patient 30 lying on bed 20 and are connected by short high resistance leads 50 to an ECG electronics sensor module 60 located in the tunnel. Two fiber optic cables 80 connect ECG electronics sensor module 60 to ECG monitor 90 located outside the MRI tunnel but elsewhere within shielded room 100. ECG monitor 90 can also be placed outside shielded room 100 by passing fiber optic cables 80 through a quarter wave guide installed in the wall of shielded room 100.

Figure 2:
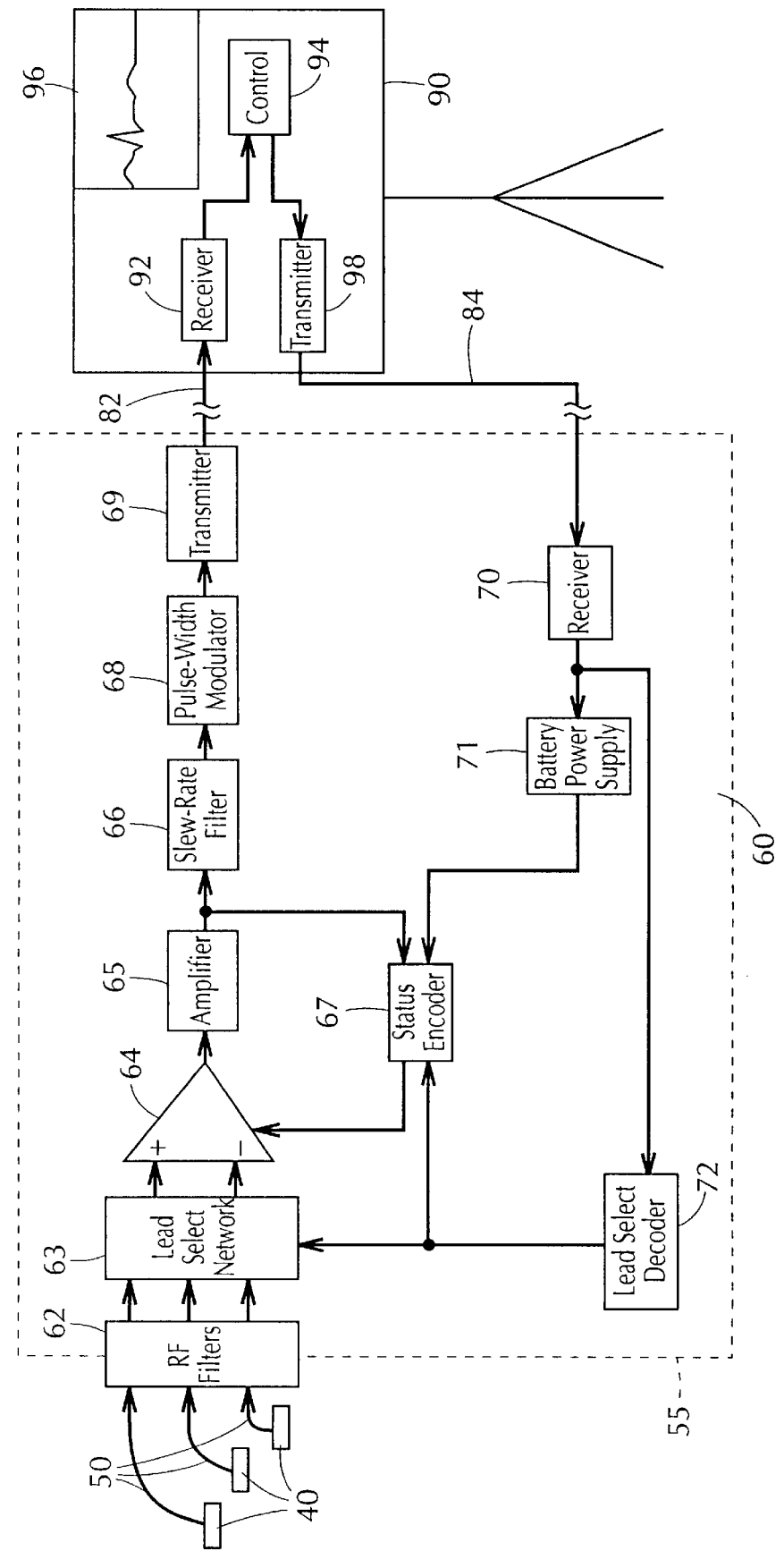
FIG. 2 is a preferred embodiment of the ECG electronics sensor module of the present invention.

Referring to FIG. 2, three electrodes 40 are connected to the ECG electronics sensor module 60 through RF filter 62 by short high resistance leads 50. Lead lengths of up to several feet have been used previously. A preferred lead length is 12" to minimize RF heating, to minimize induced spikes from switch gradients, to allow flexibility in electrode placement for optional ECG signals, and to allow ECG electronics sensor module 60 to be optimally placed to avoid MRI image interference. Faraday shield 55 surrounds the ECG electronics sensor module 60 with RF filter 62 at the input port of Faraday shield 55. RF filter 62 and Faraday shield 55 prevent RF pulses, generated by the MRI tunnel and picked up by leads 50, from entering ECG electronics sensor module 60. RF filter 62 also prevents inference to the MRI signal from pulses generated in ECG electronics sensor module 60. It is preferable for RF filter 62 to provide attenuation in excess of 50 dB at a frequency of 8.5 MHz and 70 dB at 85 MHz. One example of an RF filter 62 for use with this invention would have a cutoff frequency of 16 kHz and an attenuation of 20 dB per decade of frequency. The use of Faraday shield 55 allows the placement of ECG electronics sensor module 60 in close proximity of patient 30, allowing optimal positioning of ECG electronics sensor module 60 and electrodes 40 separately thus reducing voltage and motion artifacts from affecting the ECG and the MRI readings and preventing interference with the MRI imaging.

The output of RF filter 62 is applied to lead select network 63 which is controlled to select a pair of filtered leads 50 as active leads, as described in detail below. The pair of active leads are input to wide band (e.g. 0.1 Hz to 20 kHz), low gain differential amplifier 64. ECG signals from the active leads are combined with a DC voltage offset, as described in detail below, produced by status encode circuit 67 and amplified by differential amplifier 64. The amplified signal drives wide band single ended amplifier 65. Together the two amplifiers provide a gain of about 400. This signal, a combination of information containing the ECG signal and DC voltage offset, is applied to slew-rate filter 66 which suppresses voltage spikes from gradient pulses picked up by electrode leads 50. Preferably, a fast recovery slew-rate filter is used which does not saturate with large induced spikes. It is preferable to set slew rate filter 66 to attenuate spikes with a slew rate greater than approximately 50 mv/msec. The signal is then input to pulse width modulator 68 which drives fiber optic transmitter 69.

The light beam from fiber optic transmitter 69, modulated by the cardiac signal and DC voltage offset is transmitted from the ECG electronics sensor module 60 and the MRI tunnel on fiber optic cable 82 to fiber optic receiver 92 in ECG monitor 90 which converts the light beam back to an electrical signal. Both the cardiac portion of the received signal and the DC voltage offset, are demodulated and processed by control 94 and displayed visually on display 96 for the operator.

The DC voltage offset is utilized to indicate, at ECG monitor 90, the status of ECG electronics sensor module 60, including battery power supply 71 charge state (e.g. low battery), active pair of leads selected and lead off indication. If, for example, one of leads 40 detaches from patient 30, the ECG signal is driven out of range (ie., maximum DC voltage offset) by a circuit in lead select network 63. The operator controls ECG electronics sensor module 60 connected to the patient by adjusting control 94 on ECG monitor 90. Control 94 can be adjusted while viewing the ECG signal to select the optimal active lead combinations to provide the best ECG signal. When three electrodes are used to monitor the ECG, three different lead combinations can be chosen to avoid artifact interference and produce the best ECG signal. When four or more electrodes are used additional lead combinations can be selected to find the best cardiac signal. This gives the operator more control of the monitoring process. Control 94 also is used to place battery power supply 71 "on" or in the standby mode for additional control of ECG electronics sensor module 60.

Control 94 drives fiber optic transmitter 98 which transmits a modulated light beam on fiber optic cable 84. The light beam is received in ECG electronics sensor module 60 and converted to control voltages by fiber optic receiver 70. These control voltages control battery power supply 71, as indicated above, and lead select decoder 72. Lead select decoder 72 is stepped by the control voltage from control 94, to control lead select 63 to select the best active lead combination. Lead select decoder 72 also provides an input signal to status encode circuit 67 which also receives an input from battery power supply 71 (battery state) and feedback from the output of wide band single ended amplifier 65 to generate the DC voltage offset which is applied as an input to differential amplifier 64.

All components in ECG electronics sensor module 60 must be non-magnetic and any electrical conductive material in ECG electronics sensor module 60, such as circuit board runs and Faraday shield 55 should be thin consistent with other performance requirements.

Although this invention uses fiber optic cables for communication between ECG electronics sensor module 60 and monitor 90, other methods of communication can be utilized, including, but not limited to, laser beams or infraed ultrasound, and RF (radio wave) at frequencies greater than approximately 400 MHz to exit the MRI tunnel. In addition, other methods of encoding and decoding the information may be employed for information transmission and reception, including but not limited to, amplitude modulation of a sine wave, frequency modulation of a sine wave, frequency modulation of a pulse train, and digital communications.

Although the present invention has been shown and described with respect to preferred embodiments, various changes and modifications which are obvious to a person skilled in the art of which the invention pertains are deemed to lie within the spirit and scope of the invention. Thus numerous changes and modifications can be made while staying within the scope of the invention which is set forth in the appended claims.

We claim:

1. An electrocardiograph ("ECG") sensor and sensor control system for use with magnetic resonance imaging machines ("MRI"), to minimize artifacts in both the MRI and ECG signals comprising:

a) an ECG electronics sensor module which generates an output signal in response to a patient's ECG including at least one RF filter, a lead select network coupled to said RF filter, an amplifier coupled to said lead select network, a slew rate filter coupled to said amplifier, a pulse width modulator and a fiber optic transmitter coupled to said slew rate filter, a status encode circuit having an output and at least one input, said output of said status encode circuit coupled to said amplifier, a first input of said status encode circuit coupled to the output of said amplifier, a lead select decoder having an input and an output, said output of said lead select decoder connected to both said lead select network and to a second input of said status encode circuit, a battery power supply connected to a third input of said status encode circuit, and a fiber optic receiver connected to said battery power supply and said input of said lead select decoder;

b) a Faraday shield surrounding said ECG electronics sensor module;

c) at least three electrodes;

d) at least three high resistant leads for coupling each of said electrodes and said RF filter;

e) an ECG monitor having a fiber optic receiver and transmitter, a display and a control means for controlling and processing information received from said ECG electronics sensor module; and f) at least one first fiber optic cable coupling said fiber optic transmitter of said ECG electronic sensor module and said fiber optic receiver of said ECG monitor and at least one second fiber optic cable coupling said fiber optic transmitter of said ECG monitor to said fiber optic receiver of said ECG electronic sensor module.

2. An electrocardiograph ("ECG") sensor and sensor control system for use with magnetic resonance imaging machines ("MRI"), to minimize artifacts in both the MRI and ECG signals, comprising:

a) an ECG electronics sensor module which generates an output signal in response to a patient's ECG including at least one RF filter, a lead select network coupled to said RF filter, an amplifier coupled to said lead select network, a slew rate filter coupled to said amplifier, an encoding means for encoding said output signal and a transmitting means for transmitting said output signal coupled to said slew rate filter, a status encode circuit having an output and at least one input, said output of said status encode circuit coupled to said amplifier, a first input of said status encode circuit coupled to an output of said amplifier, a lead select decoder having an input and an output, said output of said lead select decoder coupled to both said lead select network and to a second input of said status encode circuit, a battery power supply coupled to a third input of said status encode circuit, and a receiving means for receiving a control signal coupled to said battery power supply and said input of said lead select decoder;

b) a Faraday Shield surrounding said ECG electronics sensor module;

c) at least three electrodes;

d) at least three high resistant leads for coupling each of said electrodes and said RF filter; and e) an ECG monitor having a receiving means for receiving said output signal from said ECG electronics sensor module, a transmitting means for transmitting said control signal to said ECG electronics sensor module, a control means for processing said output signal received from said ECG electronics sensor module and for controlling said control voltage transmitted to said ECG electronics sensor module, and a display means for viewing said output signal.

3. The system of claim 2, wherein said output signal comprises an ECG signal and a DC voltage offset.

4. The system of claim 3, wherein said amplifier comprises a wide band low gain differential amplifier and a wide band single ended amplifier.

5. The system of claim 4, wherein said wide band low differential gain amplifier has a bandwidth of 0.1 Hz. to 20 kHz.

6. The system of claim 5, wherein said RF filter has a cutoff frequency of 16 kHz. and an attenuation of 20 dB per decade of frequency.

7. The system of claim 6, wherein said slew rate filter attenuates spikes with a slew rate greater than 50 mv/msec.

8. An electrocardiograph ("ECG") sensor and sensor control system for use with magnetic resonance imaging machines ("MRI"), to minimize artifacts in both the MRI and ECG signals, comprising:

a) an ECG electronics sensor module which generates an output signal in response to a patient's ECG including at least one RF filter, a lead select network coupled to said RF filter, an amplifier coupled to said lead select network, an encoding means for encoding said output signal and a transmitting means for transmitting said output signal coupled to said amplifier, a lead and battery status encode circuit having an output and at least one input, said output of said lead and battery status encode circuit coupled to said amplifier, a first input of said lead and battery status encode circuit coupled to an output of said amplifier, a lead select decoder having an input and an output, said output of said lead select decoder coupled to both said lead select network and to a second input of said lead and battery status encode circuit, a battery power supply coupled to a third input of said lead and battery status encode circuit, a receiving means for receiving a control signal coupled to said battery power supply and said input of said lead select decoder;

b) a Faraday Shield surrounding said ECG electronics sensor module;

c) at least three electrodes coupled to said RF filter; and d) an ECG monitor having a receiving means for receiving said output signal from said ECG electronics sensor module, a transmitting means for transmitting said control signal to said ECG electronics sensor module, a control means for processing said output signal received from said ECG electronics sensor module and for controlling said control signal transmitted to said ECG electronics sensor module, and a display means for viewing said output signal.

9. The system of claim 8, wherein said lead and battery status encode circuit provides a status signal indicating at least one of low battery condition, lead select or lead off condition.

10. An electrocardiograph ("ECG") sensor and sensor control system for use with magnetic resonance imaging machines ("MRI") to minimize artifacts in both the MRI and ECG signals comprising:

a) an ECG electronics sensor module which generates an output signal in response to a patient's ECG including a lead select network, an amplifier coupled to said lead select network, a first transmitter coupled to said amplifier, a status encode circuit having an output and at least one input, said output of said status encode circuit coupled to said amplifier, a first input of said status encode circuit coupled to the output of said amplifier, a lead select decoder having an input and an output, said output of said lead select decoder connected to both said lead select network and to a second input of said status encode circuit, and a first receiver coupled to said input of said lead select decoder;

b) at least three electrodes coupled to said lead select network; and c) an ECG monitor having a second receiver, a second transmitter, and a controller coupled to said second receiver and said second transmitter for processing information received from said ECG electronics sensor module and for controlling said lead select network.

11. An electrocardiograph ("ECG") sensor and sensor control system for use with magnetic resonance imaging machines ("MRI") to minimize artifacts in both the MRI and ECG signals comprising:

a) an ECG electronics sensor module which generates an output signal in response to a patient's ECG including a lead select network, an amplifier coupled to said lead select network, a first transmitter coupled to said amplifier, a lead select decoder having an input and an output, said output of said lead select decoder connected to said lead select network, and a first receiver coupled to said input of said lead select decoder;

b) at least three electrodes coupled to said lead select network; and c) an ECG monitor having a second receiver, a second transmitter, and a controller coupled to said second receiver and said second transmitter for processing information received from said ECG electronics sensor module and for controlling said lead select network.

12. The ECG sensor and sensor control system of claim 11, wherein said ECG electronics sensor module further includes a status encode circuit having an output and at least one input, said output of said status encode circuit coupled to said amplifier, a first input of said status encode circuit coupled to the output of said amplifier.

13. The ECG sensor and sensor control system of claim 11, wherein said status encode circuit includes a second input connected to the output of said lead select decoder.

14. The ECG sensor and sensor control system of claim 11, wherein ECG electronics sensor further includes a battery power supply and said status encode circuit includes a second input connected to the output of said battery power supply.

15. The ECG sensor and sensor control system of claim 14, wherein said battery power supply includes a control line input which is connected to said first receiver.

16. The ECG sensor and sensor control system of claim 11, wherein said ECG electronics sensor module further includes means for providing a signal representing the status of the leads connected to the patient.

17. The ECG sensor and sensor control system of claim 11, wherein said ECG electronics sensor module further includes a battery and means for providing a signal representing the status of the charge on said battery.

* * * * *